(12) United States Patent
De La Rosa et al.

(10) Patent No.: US 11,478,511 B2
(45) Date of Patent: *Oct. 25, 2022

(54) LYMPHOCYTE BIOMARKERS FOR DETERMINING THE CLINICAL RESPONSE TO CELL THERAPY

(71) Applicant: TiGenix S.A.U, Tres Cantos - Madrid (ES)

(72) Inventors: Olga De La Rosa, Tres Cantos - Madrid (ES); Eleuterio Lombardo, Tres Cantos - Madrid (ES); Wilfried Dalemans, Leuven (BE)

(73) Assignee: TAKEDA PHARMACEUTICAL COMPANY LIMITED

( * ) Notice: Subject to any disclaimer, the term of this patent is extended or adjusted under 35 U.S.C. 154(b) by 280 days.

This patent is subject to a terminal disclaimer.

(21) Appl. No.: 16/854,294

(22) Filed: Apr. 21, 2020

(65) Prior Publication Data
US 2020/0261511 A1 Aug. 20, 2020

Related U.S. Application Data

(63) Continuation of application No. 14/776,233, filed as application No. PCT/EP2014/055282 on Mar. 17, 2014, now Pat. No. 10,660,920.

(30) Foreign Application Priority Data

Mar. 15, 2013 (EP) ...................................... 13382091

(51) Int. Cl.
*A61K 35/35* (2015.01)
*A61K 35/28* (2015.01)
*A61K 35/33* (2015.01)
*A61K 35/17* (2015.01)
*G01N 33/569* (2006.01)

(52) U.S. Cl.
CPC .............. *A61K 35/35* (2013.01); *A61K 35/17* (2013.01); *A61K 35/28* (2013.01); *A61K 35/33* (2013.01); *G01N 33/56972* (2013.01); *G01N 2333/70514* (2013.01); *G01N 2333/70517* (2013.01); *G01N 2333/70539* (2013.01); *G01N 2800/52* (2013.01)

(58) Field of Classification Search
None
See application file for complete search history.

(56) References Cited

U.S. PATENT DOCUMENTS 10,660,920 B2    5/2020   De La Rosa et al.

FOREIGN PATENT DOCUMENTS

WO        2012154344 A1   11/2012

OTHER PUBLICATIONS

Weng et al., Bone Marrow Transplantation 45: 1732-1740 (2010).*
(Continued)

*Primary Examiner* — Erin M. Bowers
(74) *Attorney, Agent, or Firm* — Tristan A. Fuierer; Casimir Jones, S.C.

(57) ABSTRACT

The present invention provides a method for determining the clinical prognosis of a human subject to the administration of a pharmaceutical composition comprising of stem cells (preferably mesenchymal stem cells), stromal cells, regulatory T-cells, fibroblasts and combinations thereof.

16 Claims, 2 Drawing Sheets

(56) References Cited

OTHER PUBLICATIONS

Yanez et al., Stem Cells 24: 2582-2591 (2006).*
Delarosa, Olga, et al.; "Mesenchymal stem cells as therapeutic agents of inflammatory and autoimmune diseases," Current Opinion in Biotechnology, 2012, pp. 978-983, vol. 23.
Clinical & Investigative Sciences Group; "Conditioning Protocols—allogeneic transplantation," www.imperial.nhs.uk/prdcons/groups/public/@clinical/@cancer/documents/doc/hhnt_005219.pdf, Sep. 23, 2012.
Krampera, Mauro, et al.; "Role for Interferon-gamma in the immunomodulatory activity of human bone marrow mesenchymal stem cells," Stem Cells, 2006, pp. 386-398, vol. 24.
Krampera, Mauro; "Mesenchymal stromal cell 'licensing': a multistep process," Leukemia, 2011, pp. 1408-1414, vol. 25.
Wang, Dandan, et al; "A CD8 T Cell-IFN-gamma-IDO Axis Is Required for Mesenchymal Stem Cell Suppression of Human SLE," Arthritis & Rheumatism, 2013, pp. S674-S675, vol. 65.
Delarosa, Olga, et al.; "Requirement of IFN-gamma-Mediated Indoleamine 2,3-Dioxygenase Expression in the Modulation of Lymphocyte Proliferation by Human Adipose-Derived Stem Cells," Tissue Engineering, 2009, pp. 2795-2806, vol. 15.
International Search Report, dated Feb. 18, 2015.
Liu, Yi, et al.; "Mesenchymal Stem Cell-Based Tissue Regeneration is Governed by Recipient T Lymphocyte via IFN-y and TNF-alpha," Nat Med, 2012, pp. 1594-1601.
Duijvestein, Marjolijn, et al.; "Autologous bone marrow-derived mesenchymal stromal cell treatment for refractory luminal Crohn's disease: results of a phase I study," Gut, 2010, pp. 1662-1669, vol. 59.
Ciccocioppo, Rachele, et al.; "Autologous bone marrow-derived mesenchymal stromal cells in the treatment of fistulising Crohn's disease," Gut, 2011, pp. 788-798, vol. 60.
García-Olmo Damián, et al.; "A Phase I Clinical Trial of the Treatment of Crohn's Fistula by Adipose Mesenchymal Stem Cell Transplantation," Dis Colon Rectum, 2005, pp. 1416-1423, vol. 48.
IPOS Second Written Opinion, Jul. 17, 2017, Singapore Patent Application No. 11201507521U.
Yanñz, et al.; Stem Cells 24: 2582-2591 (2006).
Japanese Office Action, dated Sep. 1, 2020.
Buravkova, L.B., et al.; "Subpopulation Composition and Activation of T Lymphocytes during Coculturing with Mesenchymal Stromal Cells in Medium with Different O2 Content," Bulletin of Experimental Biology and Medicine, 2011, vol. 151, pp. 344-346.
Zheng, Z.H., et al.; "Allogeneic mesenchymal stem cell and mesenchymal stem cell-differentiated chondrocyte suppress the responses of type II collagen-reactive T cells in rheumatoid arthritis," Rheumatology, 2008, vol. 47, pp. 22-30; doi: 10.1093/rheumatology/kem284.
Ringdén, Olle, et al.; Mesenchymal Stem Cells for Treatment of Therapy-Resistant Graft-versus-Host Disease, Transplantation, 2006, vol. 81 pp. 1390-1397.
Garcia-Olmo,M.D., Damian, et al.; "Expanded Adipose-Derived Stem Cells for the Treatment of Complex Perianal Fistula: a Phase II Clinical Trial," Diseases of the Colon & Rectum, 2009, vol. 52, pp. 79-86.

* cited by examiner

LYMPHOCYTE BIOMARKERS FOR DETERMINING THE CLINICAL RESPONSE TO CELL THERAPY

CROSS-REFERENCE TO RELATED APPLICATIONS

This application is filed under the provisions of 35 U.S.C. § 120 and is a continuation of U.S. patent application Ser. No. 14/776,233 filed on Sep. 14, 2015, now U.S. Pat. No. 10,660,920, which claims the priority of International Patent Application No. PCT/EP2014/055282 filed on 17 Mar. 2014 entitled "LYMPHOCYTE BIOMARKERS FOR DETERMINING THE CLINICAL RESPONSE TO CELL THERAPY" in the name of Olga DE LA ROSA, et al., which claims priority to European Patent Application No. 13382091.0 filed on 15 Mar. 2013, all of which are hereby incorporated by reference herein in their entirety.

BACKGROUND OF THE INVENTION

Adult mesenchymal stem cells (hereinafter also referred to as "MSCs" or "MSC") have been found in a variety of adult tissues. Having been first identified in the bone marrow, MSCs are now accepted to reside in other tissues of mesodermal origin: adipose tissue, placenta, umbilical cord, dental pulp, synovium. Despite ample efforts, no exclusive individual surface markers have been identified for MSCs. MSCs are defined according to the three criteria of the International Society for Cellular Therapy: a) Adhesion to plastic: MSCs can be isolated by adhesion to plastic and expanded in vitro in serum containing media with no additional requirements for growth factors or cytokines; b) Expression of a specific combination of surface markers: MSCs are negative for hematopoetic and endothelial markers such as CD11b, CD14, CD31, CD34 and CD45, and positive for a variety of other markers, including HLA class I, CD73, CD90 and CD105; c) Differentiation potential: MSCs can be identified in vitro by their ability to differentiate into mesenchymal-type cells (e.g. trilineage differentiation into adipocytes, osteoblasts and chondrocytes). MSCs are at least tripotent at early stages which may be reduced to e.g. bipotent or unipotent cells in the course of in vitro expansion processes. Although sharing these main characteristics, differences between MSCs from different sources can be found. Accordingly, the secretome differs between cell types, and bone marrow-derived MSCs (BM-MSCs) and adipose-derived MSCs (ASCs) show specific RNA and protein expression profiles.

MSCs are considered a promising tool for cell therapy in regenerative medicine, or for treating other diseases such as ischemic, inflammatory and immune diseases. Although in situ differentiation was initially thought to be the basis of their therapeutic properties (i.e. structural tissue regeneration), it is now believed that their immunomodulatory capacity and paracrine effects through trophic factors with anti-fibrotic, anti-apoptotic or pro-angiogenic properties are the more likely mechanisms of their therapeutic effect.

MSCs show immunomodulating properties and regulate the function (proliferation, activation and effector function) of a broad variety of immune cells including B lymphocytes, T lymphocytes, NK cells, monocyte-derived dendritic cells and neutrophils. The specific molecular and cellular mechanisms involved in the immunoregulatory activity of MSCs are still under investigation but rely on both cell contact-dependent mechanisms (i.e. through Jagged1-Notch1 interaction) and paracrine effects through the release of soluble factors including hepatocyte growth factor (HGF), prostaglandin-E2 (PGE2), transforming growth factor (TGF)-beta 1, indoleamine 2,3-dioxygenase (IDO), nitric oxide (NO), interleukin (IL)-10, IL-6, heme oxygenase-1 (HO-1) or HLA-G5. Furthermore, MSCs may also modulate immune responses through the generation of Regulatory T cells (Tregs). These cells are defined by the expression of CD4, CD25 and the transcription factor Forkhead box p3 (Foxp3), and play a central role in protecting from autoimmunity through their immunosupressive capacity.

In addition to this immunomodulatory capacity, an additional potential advantage of the clinical use of MSC is that the immunogenicity of MSC is considered to be low. This is due to the fact that the expression of HLA class I is low, and HLA class II and the classic co-stimulatory molecules CD40, CD80 and CD86 are not detectable.

One of the first reported (1995) clinical trials involving MSC was the bone marrow derived stromal progenitor cell therapy in the treatment of patients having hematologic malignancies. Since then numerous clinical trials have been carried out and the first marketing authorizations have been granted for MSC therapies. Currently there are several hundred trials reported involving MSC, for the treatment of indications including bone disorders (e.g. bone cysts, cleft palate, osteonecritis, spinal fusion), cartilage disorders (e.g. articular cartilage repair and meniscus repair), hematologic disorders (e.g. anemia, myelodysplastic syndrome), metabolic diseases (e.g. Type I & II diabetes), liver diseases (e.g. cirrhosis & failure), cardiovascular diseases (e.g. AMI), gastrointestinal disorders (e.g. IBD and anal fistula), autoimmune disorders (e.g. rheumatoid arthritis and Crohn's disease), pulmonary diseases (e.g. COPD and IPF), neurological diseases (e.g. MS, stroke and disc degeneration), renal diseases (e.g. kidney failure and renal transplant), urogenital disorders (e.g. urinary incontinence & erectile disfunction) and opthalogical diseases (e.g. retinitis pigmentosa).

While such on-going investigations illustrate the potential of mesenchymal stem cells in treating a wide variety of diseases and disorders the use of biomarkers for the prediction of treatment response may potentially aid in the development and use of such therapies.

SUMMARY OF THE INVENTION

The present invention provides novel blood based markers for predicting clinical response to a pharmaceutical composition comprising of stem cells (preferably mesenchymal stem cells), stromal cells, regulatory T-cells, fibroblasts and combinations thereof (e.g. multipotent stromal or stromal stem cells). In one embodiment said markers are CD3+ cells. In one embodiment said markers are selected from the group comprising CD4+ lymphocyte level, CD8+ lymphocyte level, lymphocyte HLA-II level and combinations thereof. Further aspects of the invention provide methods for treating human subjects.

DETAILED DESCRIPTION OF THE INVENTION

Definitions

Figure 1:
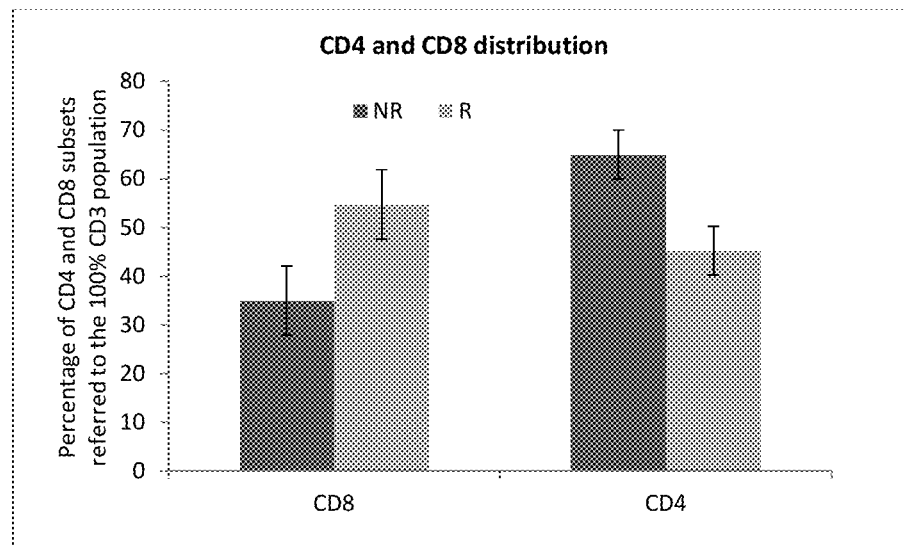
FIG. 1: CD4% and CD8% in patient PBMC in responder and non-responder groups at baseline

In order to facilitate the understanding of the present description, the meaning of some terms and expressions in the context of the invention will be explained below. Further definitions will be included throughout the description as necessary.

The terms "stem cells", "stromal cells", "regulatory T-cells" and "fibroblast cells" shall be taken to encompass the progeny thereof, including but not limited to ex-vivo cultured descendants thereof. It will be understood that progeny cells may be obtained after any number of passages from the parental population. However, in certain embodiments, the progeny cells may be obtained after about 2, about 3, about 4, about 5, about 6, about 7, about 8, about 9, or about 10 passages from the parental population.

The term "allogeneic" as used herein shall be taken to mean from different individuals of the same species. Two or more individuals are said to be allogeneic to one another when the genes at one or more loci are not identical.

The term "autologous" as used herein shall be taken to mean from the same individual.

The term "autoimmune disorders" refers to a condition in a subject characterized by cellular, tissue and/or organ injury caused by an inmunological reaction of the subject to its own cells, tissues and/or organs. Illustrative, non-limiting examples of autoimmune diseases which can be treated with the methods or pharmaceutical compositions of the invention include alopecia areata, ankylosing spondylitis, antiphospholipid syndrome, autoinmmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, Anti-Glomerular Basement Membrane Disease, Antiphospholipid Syndrome, Autoimmune Diseases of the Nervous System, Familial Mediterranean Fever, Lambert-Eaton Myasthenic Syndrome, Sympathetic Ophthalmia, Polyendocrinopathies, Psoriasis, etc.

For the purposes of the invention described herein, "immune disorders" include autoimmune diseases and immunologically mediated diseases such as but not limited to immune-mediated inflammatory diseases.

The term "inflammatory disease" refers to a condition in a subject characterized by inflammation, e.g. chronic inflammation. Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

The term "isolated" applied to a cell population refers to a cell population, isolated from the human or animal body, which is substantially free of one or more cell populations that are associated with said cell population in vivo or in vitro. The term "MHC" (major histocompatibility complex) refers to a subset of genes that encodes cell-surface antigen-presenting proteins. In humans, these genes are referred to as human leukocyte antigen (HLA) genes. Herein, the abbreviations MHC or HLA are used interchangeably. The term "subject" refers to an animal, preferably a mammal including a non-primate (e.g., a cow, pig, horse, cat, dog, rat, or mouse) and a primate (e.g., a monkey, or a human). In a preferred embodiment, the subject is a human.

The term "immunomodulatory" refers to the inhibition or reduction of one or more biological activities of the immune system which includes, but is not limited to, downregulation of immune response and inflammatory states as well as changes in cytokine profile, cytotoxic activity and antibody production. The term "antigen specific immunomodulatory" refers to the inhibition or reduction of one or more biological activities of the immune system associated with a specific antigen or antigens, including both alloantigens and autoantigens. The term "immunomodulatory" shall be taken to comprise "antigen specific immunomodulatory".

As used herein, "negative" or "−" as used with respect to cell surface markers shall be taken to mean that mean that, in a cell population, less than 20%, 10%, preferably less than 9%, 8%, 7%, 6%, 59%, 4%, 3%, 2%, 1% or none of the cells express said marker. Expression of cell surface markers may be determined for example by means of flow cytometry for a specific cell surface marker using conventional methods and apparatus (for example a Beckman Coulter Epics XL FACS system used with commercially available antibodies and standard protocols known in the art).

As used herein the term "mesenchymal stem cell" (also referred to herein as "MSC") shall be taken to mean a stromal cell which is capable of giving rise to multiple different types of cell, originally derived from the mesenchyme. The term refers to a cell which is capable of differentiating into at least one of an osteoblast, a chondrocyte, an adipocyte, or a myocyte. The term as used herein shall be taken to include the progeny of said MSC, for example but not limited to subcultured descendants thereof.

As used herein, the expression "significant expression" or its equivalent terms "positive" and "+" when used in regard to a cell surface marker shall be taken to mean that, in a cell population, more than 20%, preferably more than, 30%, 40%, 50%, 60%, 70%, 80%, 90%, 95%, 98%, 99% or even all of the cells of the cells express said marker.

Expression of cell surface markers may be determined for example by means of flow cytometry for a specific cell surface marker using conventional methods and apparatus (for example a Beckman Coulter Epics XL FACS system used with commercially available antibodies and standard protocols known in the art) that show a signal for a specific cell surface marker in flow cytometry above the background signal using conventional methods and apparatus (for example, a Beckman Coulter Epics XL FACS system used with commercially available antibodies and standard protocols known in the art). The background signal is defined as the signal intensity given by a non-specific antibody of the same isotype as the specific antibody used to detect each surface marker in conventional FACS analysis. For a marker to be considered positive the specific signal observed is stronger than 20%, preferably stronger than, 30%, 40%, 50%, 60%, 70%, 80%, 90%, 500%, 1000%, 5000%, 10000% or above, than the background signal intensity using conventional methods and apparatus (for example a Beckman Coulter Epics XL FACS system used with commercially available antibodies and standard protocols known in the art).

Furthermore, commercially available and known monoclonal antibodies against said cell-surface markers (e.g., cellular receptors and transmembrane proteins) can be used to identity relevant cells.

The term "connective tissue" refers to tissue derived from mesenchyme and includes several tissues which are characterized in that their cells are included within the extracellular matrix. Examples of connective tissues include but are not limited to, adipose and cartilaginous tissues.

The term "fibroblast" as used herein shall be taken to include fibroblast like synovial cells.

As used herein, the terms "treat", "treatment" and "treating" when used directly in reference to a patient or subject shall be taken to mean the administration of a pharmaceutical composition to a subject in need of said treatment for the amelioration of one or more symptoms associated with a disease or disorder (including, but not limited to, an ischemic disease, an inflammatory disorder, an autoimmune disease or an immunologically mediated disease including rejection of transplanted organs and tissues).

The terms "clinical responsiveness", "clinical response" and "treatment response" shall be taken to mean change of one or more symptoms associated with a disease or disorder including, but not limited to, an ischemic disease, an inflammatory disorder, an autoimmune disease or an immunologically mediated disease including rejection of transplanted organs and tissues, wherein said change results from the administration of a pharmaceutical composition to a subject in need of said treatment.

The term "responder" shall be taken to mean an individual, subject or patient having a disease or disorder (including, but not limited to, an ischemic disease, an inflammatory disorder, an autoinmmune disease or an immunologically mediated disease including rejection of transplanted organs and tissues) wherein a treatment ameliorates or improves one or more symptoms thereof or otherwise provides therapeutic benefit wherein said change results from the administration of a pharmaceutical composition to a subject in need of said treatment.

The term "tissue damage" as used herein shall be taken to include both soft tissue injury and hard tissue injury and shall be taken include fistula e.g. anal fistula, rectovaginal fistula etc.

As used herein the terms "treat" and "treating" when used directly in reference to damaged tissues shall be taken to mean the amelioration of such damage by both direct mechanisms such as the regeneration of damaged tissues, repair or replacemement of damaged tissues (e.g. by scar tissue) as well as through indirect mechanisms e.g., reducing inflammation thereby enabling tissue formation.

The term "combination therapy" refers to the use of the pharmaceutical compositions of the present invention together with other active agents or treatment modalities, in the manner of the present invention for the amelioration of one or more symptoms associated with a disorder including, but not limited to, an inflammatory disorder, an autoimmune disease or an immunologically mediated disease including rejection of transplanted organs and tissues. These other agents or treatments may include known drugs and therapies for the treatment of such disorders such as but not limited to corticosteroids and non-steroidal anti-inflammatory compounds.

Prognostic Methods.

The present invention provides a method for predicting treatment response to a cellular therapy in patients suffering from tissue damage, ischemic, inflammatory and/or an immune disorder by evaluating a blood-based marker, preferably lymphocytes. In a preferred embodiment said "cellular therapy" is the administration of a pharmaceutical composition comprising of stem cells (preferably mesenchymal stem cells), stromal cells, regulatory T-cells, fibroblasts and combinations thereof (e.g. multipotent stromal or stromal stem cells). In one embodiment thereof said patient is a human subject having tissue damage, ischemic, inflammatory and/or immune disorders. Accordingly the invention provides a method for predicting clinical response to the administration of a pharmaceutical composition comprising of stem cells (preferably mesenchymal stem cells), stromal cells, regulatory T-cells, fibroblasts and combinations thereof (e.g. multipotent stromal or stromal stem cells) in a human subject having tissue damage, ischemic, inflammatory and/or immune disorders. In one embodiment the method comprises measuring lymphocytes or CD3+ cell populations in a blood sample obtained from said human subject and predicting therefrom clinical responsiveness to the administration of a pharmaceutical composition comprising of stem cells (preferably mesenchymal stem cells), stromal cells, regulatory T-cells, fibroblasts and combinations thereof (e.g. multipotent stromal or stromal stem cells).

In one embodiment the method comprises evaluating a marker selected from the group comprising CD4+ lymphocyte level, CD8+ lymphocyte level, lymphocyte HLA-II level and combinations thereof in a blood sample obtained from said human subject and predicting therefrom clinical responsiveness to the administration of a pharmaceutical composition comprising of stem cells (preferably mesenchymal stem cells), stromal cells, regulatory T-cells, fibroblasts and combinations thereof (e.g. multipotent stromal or stromal stem cells).

In one embodiment the pharmaceutical composition comprises mesenchymal stromal and/or stem cells e.g. multipotent stromal or stromal stem cells. In one embodiment the pharmaceutical composition comprises adipose derived mesenchymal stromal and/or stem cells.

In one embodiment the CD4+, CD8+ or HLA-II level is measured in a human subject PBMC. In one embodiment the CD4+, CD8+ or HLA-II level is measured in human subject lymphocytes. In one embodiment the CD4+, CD8+ or HLA-II level is measured in human subject CD3+ lymphocytes.

In one embodiment the CD4+, CD8+ or HLA-II level may be determined as a % of total lymphocyte population, number of cells or ratio.

In an embodiment the marker is CD4+ level. In a further embodiment a CD4+ level equal to or less than a value in the range of 35% to 55%, more preferably 40% to 50% (e.g. less than about 35%; less than about 40%; less than about 45%; less than about 50%; less than about 55%) CD4+ cells within the T-lymphocyte population is associated with a human subject predicted to be a responder.

In an embodiment the marker is CD8+ level. In a further embodiment a CD8+ level equal to or greater than a value in the range of 45% to 65%, more preferably 50%-60% (e.g. more than about 45%; more than about 50%; more than about 55%; more than about 60%; more than about 65%) CD8+ cells within the T-lymphocyte population is associated with a human subject predicted to be a responder.

In an embodiment the marker is the CD4+:CD8+ cell ratio. In a further embodiment a CD4+:CD8+ cell ratio equal to or lower than 1.5, more preferably equal to or lower than a value in the range of 1.2 to 0.5, most preferably equal to or lower than 1 (e.g. less than about 1.2; less than about 1.1; less than about 1; less than about 0.9; less than about 0.8; less than about 0.7; less than about 0.6) is associated with a human subject predicted to be a responder.

In an embodiment the marker is HLA-II level. In a further embodiment a reduction in lymphocyte HLA-II level after contact thereof with allogeneic mesenchymal stem cells is associated with a human subject predicted to be a responder.

The HLA-II level is considered reduced when its levels decrease with respect to a reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., absent).

The reference value used to determine whether the HLA-II level is reduced is, for instance, the HLA-II level in lymphocytes not stimulated with allogeneic stem cells. Moreover, the HLA-II level in non-stimulated lymphocytes can be determined in a sample from the same patient which is going to be treated. Alternatively it is also possible to obtain the reference value from lymphocytes from a different individual or from lymphocytes pooled from the blood of a population of two or more individuals. The population, for example, can comprise 3, 4, 5, 10, 15, 20, 30, 40, 50 or more individuals.

In one embodiment the CD4+, CD8+ or HLA-II level is measured prior to administration of the pharmaceutical composition. In a further embodiment the CD4+, CD8+ or HLA-II level is measured subsequent to administration of the pharmaceutical composition. In one embodiment the CD4+, CD8+ or HLA-II level is measured at least 1, 5, 10, 15 or 20 days after administration of the pharmaceutical composition. In one embodiment the CD4+, CD8+ or HLA-II level is measured both prior to and subsequent to administration of the pharmaceutical composition. In another embodiment wherein the pharmaceutical composition is administered a plurality of times to the patient the CD4+, CD8+ or HLA-II level is measured prior to and/or subsequent to administration of the pharmaceutical composition.

Treatment Methods.

The present invention provides a method for treating a human subject having tissue damage, ischemic, inflammatory and/or immune disorders with a pharmaceutical composition comprising of stem cells (preferably mesenchymal stem cells), stromal cells, regulatory T-cells, fibroblasts and combinations thereof (e.g. multipotent stromal or stromal stem cells).

In one embodiment the method comprises i) determining whether the patient is a responder or a non-responder to said pharmaceutical composition by measuring CD3+ cell populations in a blood sample obtained from said human subject and ii) administering said pharmaceutical composition only if the human subject is determined to be a responder.

In one embodiment the method comprises i) determining whether the patient is a responder or a non-responder to said pharmaceutical composition by evaluating a marker selected from the group comprising CD4+ lymphocyte level, CD8+ lymphocyte level, lymphocyte HLA-II level and combinations thereof in a blood sample obtained from said human subject and ii) administering said pharmaceutical composition only if the human subject is determined to be a responder.

In one embodiment the patient has not previously been treated with a pharmaceutical composition comprising of stem cells (preferably mesenchymal stem cells), stromal cells, regulatory T-cells, fibroblasts and combinations thereof (e.g. multipotent stromal or stromal stem cells). In an alternative embodiment the patient is administered a pharmaceutical composition comprising of stem cells (preferably mesenchymal stem cells), stromal cells, regulatory T-cells, fibroblasts and combinations (e.g. multipotent stromal or stromal stem cells) thereof prior to i) and administration of said pharmaceutical composition is only continued or a subsequent dose thereof is only adminstered if the human subject is identified as a responder.

In one embodiment the pharmaceutical composition comprises mesenchymal stromal and/or stem cells e.g. multipotent stromal or stromal stem cells. In one embodiment the pharmaceutical composition comprises adipose derived mesenchymal stromal and/or stem cells. In a further embodiment said mesenchymal stromal and/or stem cells are expanded prior to i).

In one embodiment the CD4+, CD8+ or HLA-II level is measured in patient PBMC. In one embodiment the CD4+, CD8+ or HLA-II level is measured in patient lymphocytes. In one embodiment the CD4+, CD8+ or HLA-II level is measured in human subject CD3+ lymphocytes.

In one embodiment the CD4+, CD8+ or HLA-II level may be determined as a % of total lymphocyte population, number of cells or ratio.

In an embodiment the marker is CD4+ level. In a further embodiment a CD4+ level equal to or less than a value in the range of 35% to 55%, more preferably 40% to 50% (e.g. less than about 35%; less than about 40%; less than about 45%; less than about 50%; less than about 55%) CD4+ cells within the T-lymphocyte population is associated with a human subject classified as a responder.

In an embodiment the marker is CD8+ level. In a further embodiment a CD8+ level equal to or greater than a value in the range of 45% to 65%, more preferably 50%-60% (e.g. more than about 45%; more than about 50%; more than about 55%; more than about 60%; more than about 65%) CD8+ cells within the T-lymphocyte population is associated with a human subject classified as a responder.

In an embodiment the marker is the CD4+:CD8+ cell ratio. In a further embodiment a CD4+:CD8+ cell ratio equal to or lower than 1.5, more preferably equal to or lower than a value in the range of 1.2 to 0.5, most preferably equal to or lower than 1 (e.g. less than about 1.2; less than about 1.1; less than about 1; less than about 0.9; less than about 0.8;

less than about 0.7; less than about 0.6) is associated with a human subject as a responder.

In an embodiment the marker is HLA-II level. In a further embodiment a reduction in lymphocyte HLA-II level after contact thereof with allogeneic mesenchymal stem cells is associated with a human subject classified as a responder.

The HLA-II level is considered reduced when its levels decrease with respect to a reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., absent).

The reference value used to determine whether the HLA-II level is reduced is, for instance, the HLA-II level in lymphocytes not stimulated with allogeneic stem cells. Moreover, the HLA-II level in non-stimulated lymphocytes can be determined in a sample from the same patient which is going to be treated. Alternatively it is also possible to obtain the reference value from lymphocytes from a different individual or from lymphocytes pooled from the blood of a population of two or more individuals. The population, for example, can comprise 3, 4, 5, 10, 15, 20, 30, 40, 50 or more individuals.

In one embodiment the CD4+, CD8+ or HLA-II level is measured prior to administration of the pharmaceutical composition. In one embodiment the CD4+, CD8+ or HLA-II level is measured at least 1, 5, 10, 15 or 20 days after administration of the pharmaceutical composition.

Medical Uses.

In one aspect the present invention provides a pharmaceutical composition comprising of stem cells (preferably mesenchymal stem cells), stromal cells, regulatory T-cells, fibroblasts and combinations thereof (e.g. multipotent stromal or stromal stem cells) for the treatment, modulation, prophylaxis, and/or amelioration of one or more symptoms associated with tissue damage, ischemic, inflammatory and/or immune disorders in a human subject.

In one embodiment the invention provides a pharmaceutical composition comprising of stem cells (preferably mesenchymal stem cells), stromal cells, regulatory T-cells, fibroblasts and combinations thereof (e.g. multipotent stromal or stromal stem cells) for treatment, modulation, prophylaxis, and/or amelioration of one or more symptoms associated with tissue damage, ischemic, inflammatory and/or immune disorders in a human subject wherein said human subject has a CD4+ level equal to or less than a value in the range of 35% to 55%, more preferably 40% to 50% (e.g. less than about 35%; less than about 40%; less than about 45%; less than about 50%; less than about 55%) of T-lymphocytes.

In a further embodiment the invention provides the use of stem cells (preferably mesenchymal stem cells), stromal cells, regulatory T-cells, fibroblasts and combinations thereof (e.g. multipotent stromal or stromal stem cells in the manufacture of a pharmaceutical composition for treatment, modulation, prophylaxis, and/or amelioration of one or more symptoms associated with tissue damage, ischemic, inflammatory and/or immune disorders in a human subject wherein said human subject has a CD4+ level equal to or less than a value in the range of 35% to 55%, more preferably 40% to 50% (e.g. less than about 35%; less than about 40%; less than about 45%; less than about 50%; less than about 55%) of T-lymphocytes.

In one embodiment the invention provides a pharmaceutical composition comprising of stem cells (preferably mesenchymal stem cells), stromal cells, regulatory T-cells, fibroblasts and combinations thereof (e.g. multipotent stromal or stromal stem cells) for treatment, modulation, prophylaxis, and/or amelioration of one or more symptoms associated with tissue damage, ischemic, inflammatory and/or immune disorders in a human subject wherein said human subject has a CD8+ level equal to or greater than a value in the range of 45% to 65%, more preferably 50%-60% (e.g. more than about 45%; more than about 50%; more than about 55%; more than about 60%; more than about 65%) of T-lymphocytes.

In a further embodiment the invention provides the use of stem cells (preferably mesenchymal stem cells), stromal cells, regulatory T-cells, fibroblasts and combinations thereof (e.g. multipotent stromal or stromal stem cells in the manufacture of a pharmaceutical composition for treatment, modulation, prophylaxis, and/or amelioration of one or more symptoms associated with tissue damage, ischemic, inflammatory and/or immune disorders in a human subject wherein said human subject has a CD8+ level equal to or greater than a value in the range of 45% to 65%, more preferably 50%-60% (e.g. more than about 45%; more than about 50%; more than about 55%; more than about 60%; more than about 65%) of T-lymphocytes.

In one embodiment the invention provides a pharmaceutical composition comprising of stem cells (preferably mesenchymal stem cells), stromal cells, regulatory T-cells, fibroblasts and combinations thereof (e.g. multipotent stromal or stromal stem cells) for treatment, modulation, prophylaxis, and/or amelioration of one or more symptoms associated with tissue damage, ischemic, inflammatory and/or immune disorders in a human subject wherein said human subject has a CD4+:CD8+ cell ratio equal to or lower than 1.5, more preferably equal to or lower than a value in the range of 1.2 to 0.5, most preferably equal to or lower than 1 (e.g. less than about 1.2; less than about 1.1; less than about 1; less than about 0.9; less than about 0.8; less than about 0.7; less than about 0.6).

In a further embodiment the invention provides the use of stem cells (preferably mesenchymal stem cells), stromal cells, regulatory T-cells, fibroblasts and combinations thereof (e.g. multipotent stromal or stromal stem cells in the manufacture of a pharmaceutical composition for treatment, modulation, prophylaxis, and/or amelioration of one or more symptoms associated with tissue damage, ischemic, inflammatory and/or immune disorders in a human subject wherein said human subject has a CD4+:CD8+ cell ratio equal to or lower than 1.5, more preferably equal to or lower than a value in the range of 1.2 to 0.5, most preferably equal to or lower than 1 (e.g. less than about 1.2; less than about 1.1; less than about 1; less than about 0.9; less than about 0.8; less than about 0.7; less than about 0.6).

In a further embodiment the invention provides the use of stem cells (preferably mesenchymal stem cells), stromal cells, regulatory T-cells, fibroblasts and combinations thereof (e.g. multipotent stromal or stromal stem cells in the manufacture of a pharmaceutical composition for treatment, modulation, prophylaxis, and/or amelioration of one or more symptoms associated with tissue damage, ischemic, inflammatory and/or immune disorders in a human subject wherein said human subject has a reduction in lymphocyte HLA-II level after contact thereof with allogeneic mesenchymal stem cells. In a preferred embodiment, the HLA-II level is considered reduced when it shows a decrease with respect to a reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., absent).

The reference value used to determine whether the HLA-II level is reduced is, for instance, the HLA-II level in lymphocytes not stimulated with allogeneic stem cells. Moreover, the HLA-II level in non-stimulated lymphocytes can be determined in a sample from the same patient which is going to be treated. Alternatively it is also possible to obtain the reference value from lymphocytes from a different individual or from lymphocytes pooled from the blood of a population of two or more individuals. The population, for example, can comprise 3, 4, 5, 10, 15, 20, 30, 40, 50 or more individuals.

In one embodiment the invention provides a pharmaceutical composition comprising of stem cells (preferably mesenchymal stem cells), stromal cells, regulatory T-cells, fibroblasts and combinations thereof (e.g. multipotent stromal or stromal stem cells) for treatment, modulation, prophylaxis, and/or amelioration of one or more symptoms associated with tissue damage, ischemic, inflammatory and/or immune disorders in a human subject wherein said human subject has a reduction in lymphocyte HLA-II level after contact thereof with allogeneic mesenchymal stem cells.

In a further embodiment the invention provides the use of stem cells (preferably mesenchymal stem cells), stromal cells, regulatory T-cells, fibroblasts and combinations thereof (e.g. multipotent stromal or stromal stem cells in the manufacture of a pharmaceutical composition for treatment, modulation, prophylaxis, and/or amelioration of one or more symptoms associated with tissue damage, ischemic, inflammatory and/or immune disorders in a human subject wherein said human subject has a reduction in lymphocyte HLA-II level after contact thereof with allogeneic mesenchymal stem cells.

Immunophenotyping.

Methods for the measurement of HLA-II+, CD4+ and CD8+ lymphocyte populations are well known in the art. The gold standard method for quantification of said cells is by flow cytometry. Staining panels are commercially available for the fluorescence tag detection of said lymphocyte cell populations. Typically % of each subpopulation is determined by staining for the specific marker within the CD3 population. Conversion of % to cell counts can be carried out by using a volumetric approach, either by analyzing a fixed volume of sample or recording the volume of any given sample. Alternatively beads-based systems allow the conversion of % to absolute cell counts by using fluorescent beads to spike samples and thus measure sample volume. The volumetric or beads-based approaches are referred to as single platform approaches, and are commercially available e.g. TruCount (Beckton Dickinson) and FlowCould (Beckton Coulter). Additionally dedicated platforms for CD4+ analysis are also available e.g. FACScount (Beckton Dickinson). An alternative methodology for lymphocyte quantification is the use of haematology analyser for measurement of total lymphocyte count as a reference for the FACS measurement. Often referred to as the "dual platform" approach, approaches such as "pan-leucogating" are known in the art for quantification of lymphocyte sub-populations using the combined platform approach. As an alternative to flow cytometry manual methods using microscopy in combination with haemocytometers are known. Commercially available kits utilize immunomagnetic beads for the isolation of cell subpopulations that may be subsequently counted under the microscope.

Pharmaceutical Compositions.

In one embodiment the pharmaceutical composition of the invention comprises a prophylactically or therapeutically effective amount of stem cells (preferably mesenchymal stem cells), stromal cells, regulatory T-cells, fibroblasts and combinations thereof (e.g. multipotent stromal or stromal stem cells) and a pharmaceutical carrier. In one embodiment the pharmaceutical composition comprises mesenchymal stem or stromal cells, more preferably adipose-derived mesenchymal stem or stromal cells.

In one embodiment a pharmaceutical composition will comprise the number of cells required for one dose; suitable cell numbers per dose are for example between about 100 and about 100 million cells; between about 1000 and about 10 million cells; between about 10,000 and about 1 million cells; between about 100 and about 1000 cells; between about 1000 and about 10,000 cells; between about 10,000-100,000 cells; between about 100,000-1 million cells; between about 1 million-10 million cells; between about 10 million-100 million cells.

Suitable pharmaceutical carriers are known in the art and are preferably those approved by a regulatory agency of the US Federal or a state government or listed in the U S Pharmacopeia, or European Pharmacopeia, or other generally recognized pharmacopeia for use in animals, and more particularly in humans. The term "carrier" refers to a diluent, adjuvant, excipient, vehicle or support with which the therapeutic agent is administered. The composition, if desired, can also contain minor amounts of pH buffering agents. Examples of suitable pharmaceutical carriers are described in "Remington's Pharmaceutical Sciences" by E W Martin. Such compositions will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the pharmaceutical compositions are sterile and in suitable form for administration to a subject, preferably an animal subject, more preferably a mammalian subject, and most preferably a human subject.

The pharmaceutical composition of the invention may be in a variety of forms. These include, for example, semi-solid, and liquid dosage forms, such as lyophilized preparations, liquid solutions or suspensions, injectable and infusible solutions, etc. The pharmaceutical composition is preferably injectable.

The pharmaceutical compositions of the invention may also be combined with other treatment modalities, e.g., corticosteroids, non-steroidal anti-inflammatory compounds, or other agents useful in treating inflammation. The combined use of the agents of the present invention with these other therapies or treatment modalities may be concurrent, or given sequentially, that is, the two treatments may be divided up such that said therapies or pharmaceutical compositions of the invention may be given prior to or after the other therapy or treatment modality. The attending physician may decide on the appropriate sequence of administering the immunomodulatory cells, or a pharmaceutical composition comprising same, in combination with other agents, therapies or treatment modalities.

It is preferred that the pharmaceutical compositions according to the present invention comprises stem cells, stromal cells regulatory T-cells and/or fibroblast cells. It is particularly preferred that said stem or stromal cells are mesenchymal stem cells (hereinafter also referred to as MSC), most preferably adipose derived stem cells (hereinafter also referred to as ASC), which are multipotent stromal cells that originate from adipose tissue, preferably from human adipose tissue (hASCs).

The MSC used in the method of the present invention are preferably derived from connective tissue, most preferably stromal tissue. In a preferred embodiment said MSC are derived from adipose tissue and in a further preferred embodiment from the stromal fraction of the adipose tissue. In an alternative embodiment, said MSC are obtained from chondrocytes of the hyaline cartilage. In a further embodiment, said MSC are obtained from skin. In another embodiment, said MSC are obtained from bone marrow.

The MSC can be obtained from any suitable source of connective tissue from any suitable animal, most preferably humans. It is preferred that said cells are obtained from non-pathological mammalian sources, preferably post-natal (e.g., rodent or primate) sources. In a preferred embodiment, the MSC are obtained from a source of connective tissue, such as, but not limited to, the stromal fraction of adipose tissue, hyaline cartilage, bone marrow or skin. Most preferably the MSC of the methods of the present invention are obtained from non-pathological, post-natal, human stromal adipose tissue.

The fibroblasts used in the present invention are mesenchyme derived connective tissue that are associated with the synthesis and maintenance of extra cellular matrix and shall be taken to include fibroblast like synovial cells. The fibroblasts can be obtained from any suitable animal, most preferably human.

The regulatory T-cells (alternatively known as suppressor T-cells) as used in the present invention may be derived from any suitable source, such as blood or spleen. The regulatory T-cells may be naturally occurring CD4+Foxp3+ cells, or they may be ex-vivo isolated and/or expanded regulatory T-cells. Methods for the ex-vivo expansion of regulatory T-cells are known in the art and include the isolation from whole blood (e.g., as part of the PBMC fraction) followed by expansion using e.g., mesenchymal stem cells or Rapamycin.

With respect to the intended recipient of the pharmaceutical compositions as administered according to the present invention, the MSC, regulatory T-cells and/or fibroblast cells may be of either allogeneic (donor) or autologous (subject) origin. In a preferred embodiment of the method said MSC, regulatory T-cells and/or fibroblast cells are of allogeneic origin.

The MSC used in the method of the present invention are preferably characterized in that (i) they do not express markers specific for antigen presenting cells, (ii) they do not express IDO (Indoleamine 2,3-Dioxygenase) constitutively, (iii) they express IDO upon stimulation with IFN-gamma, and in the case of MSC (iv) they present the capacity to be differentiated into at least two cell lineages.

MSC are multipotent stem cells and have the capacity to proliferate and be differentiated into at least two, more preferably three, four, five, six, seven or more cell lineages. Illustrative, non-limiting examples of cell lineages into which said MSC can be differentiated include osteocytes, adipocytes, chondrocytes, tenocytes, myocytes, cardiomyocytes, hematopoietic-supporting stromal cells, endothelial cells, neurons, astrocytes, and hepatocytes. MSC can proliferate and be induced differentiate into cells of other lineages by conventional methods. Methods of identifying and subsequently isolating differentiated cells from their undifferentiated counterparts can be also carried out by methods well known in the art.

Preferably the MSC are ex-vivo cultured cells, methods for the expansion of MSC populations are known in the art.

Subsequent to isolation MSC can be maintained and allowed to proliferate ex vivo in a cell culture medium. Such medium may be composed of, for example, Dulbecco's Modified Eagle's Medium (DMEM), with antibiotics (for example, 100 units/ml Penicillin and 100 µg/ml Streptomycin) or without antibiotics, and 2 mM glutamine, and supplemented with 2%-20% fetal bovine serum (FBS). It is within the skill of one in the art to modify or modulate concentrations of media and/or media supplements as necessary for the cells used. Sera often contain cellular and non-cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), porcine serum, sheep serum, rabbit serum, rat serum (RS), etc. It is also within the scope of the invention that if said MSC are of human origin, the cell culture medium is supplemented with a human serum, preferably of autologous origin. It is understood that sera can be heat-inactivated at 55-65° C. if deemed necessary to inactivate components of the complement cascade. Modulation of serum concentrations and/or withdrawal of serum from the culture medium can also be used to promote survival of one or more desired cell types. Preferably, said MSC will benefit from FBS concentrations of about 2% to about 25%. In another embodiment, the MSC can be expanded in a cell culture medium of definite composition, in which the serum is replaced by a combination of serum albumin, serum transferrin, selenium, and recombinant proteins including but not limited to insulin, platelet-derived growth factor (PDGF), and basic fibroblast growth factor (bFGF) as known in the art.

Many cell culture media already contain amino acids, however some require supplementation prior to culturing of cells. Such amino acids include, but are not limited to, L-alanine, L-arginine, L-aspartic acid, L-asparagine, L cysteine, L-cystine, L-glutamic acid, L-glutamine, L-glycine, and the like.

Antimicrobial agents are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone(R)), ampicillin, gentamicin, bleomycin, hygromacin, kanamycin, mitomycin, etc.

Hormones can also be advantageously used in cell culture and include, but are not limited to, D-aldosterone, diethylstilbestrol (DES), dexamethasone, b-estradiol, hydrocortisone, insulin, prolactin, progesterone, somatostatin/human growth hormone (HGH), etc.

In one embodiment the stem cells (preferably mesenchymal stem cells), stromal cells, regulatory T-cells, fibroblasts and combinations thereof (e.g. multipotent stromal or stromal stem cells) may have be autologous, allogeneic or xenogenic. It is particularly preferred that said stem cells (preferably mesenchymal stem cells), stromal cells, regulatory T-cells, fibroblasts and combinations thereof (e.g. multipotent stromal or stromal stem cells) are allogeneic to the patient or subject to which they are administered or intended for administration.

Expanded Cells.

In one embodiment the stem cells (preferably mesenchymal stem cells), stromal cells, regulatory T-cells, fibroblasts and combinations thereof (e.g. multipotent stromal or stromal stem cells) may have been expanded prior to use in the methods and compositions of the present invention.

In certain embodiments, the cells may be cultured for at least about 15 days, at least about 20 days, at least about 25 days, or at least about 30 days. The expansion of cells in culture may improve the homogeneity of the cell phenotype in the cell population, accordingly in a preferred embodiment said cells are cultured until substantially homogenous.

In certain embodiments, the cells are expanded in culture for at least three culture passages or "passaged at least three times". In other embodiments, the cells are passaged at least four times, at least five times, at least six times, at least seven times, at least eight times, at least nine times, or at least ten times. It is appreciated that multilineage differentiation potential of the cells may decrease during expansion, e.g. with successive passaging of the cells; such progeny cells are nonetheless within the scope of the embodiments of the present invention. Methods for cell expansion are known in the art and may comprise the use of commercially available 2D or 3D bioreactors.

Cryopreserved Cells.

In one embodiment the stem cells (preferably mesenchymal stem cells), stromal cells, regulatory T-cells, fibroblasts and combinations thereof (e.g. multipotent stromal or stromal stem cells) may have been cryopreserved and thawed prior to use in the methods and compositions of the present invention.

Methods for the cryopreservation of stem cells are known in the art and may include the use of cryopreservation buffers or medium. Such buffers are known in the art and are commercially available.

Genetically Engineered Cells

In another embodiment the MSC, regulatory T-cells and/or fibroblast cells may be genetically engineered cells (e.g. transduced or transfected with an exogenous nucleic acid), or derived therefrom.

For example said cells may be genetically engineered to constitutively express indoleamine 2,3-dioxygenase (IDO), e.g., by transfection with an appropriate nucleic acid construct encoding said enzyme and optionally a suitable promoter sequence. Genetic engineering of cells is known in the art and may be carried out by a person skilled in the art.

Irradiated Cells.

In yet another embodiment the MSC, regulatory T-cells and/or fibroblast cells may have been irradiated prior to their use in the method of the present invention. Irradiation of cells reduces their proliferative capabilities and survival times.

The irradiation may be carried out using a suitable controlled source of ionizing radiation, such a gamma irradiator device. The irradiation conditions must be experimentally adjusted by a person skilled in the art to determine the required exposure time to impart a radiation dose that causes the long term growth arrest of the MSC, regulatory T-cells and/or fibroblast cells. In one embodiment said radiation dose is within a range selected from the group consisting of 1-100 Gy; 5-85 Gy, 10-70 Gy, 12-60 Gy, however, it is particularly preferred that said radiation dose is within the range of 15-45 Gy, typically 20-30 Gy or 22-28 Gy.

CD26 Antagonist Treated Cells.

In still another embodiment the MSC, regulatory T-cells and/or fibroblast cells may be treated with a CD26 antagonist or inhibitor prior to use in the method of the present invention. CD26 antagonists and inhibitors are known in the art and include but are not limited to Aminomethylpyridine; P32/98; NVP DPP728; PSN9301; Isoleucine thiazolidide; Denagliptin; Sitagliptin; Vildagliptin; Saxagliptin; Alogliptin; Diprotin A, and such treatment may be carried out by a person skilled in the art.

IFN-Gamma Stimulated Cells.

In another embodiment the MSC, regulatory T-cells and/or fibroblast cells may be stimulated with interferon gamma prior to use in the method of the present invention. IFN-gamma treatment of MSC for the stimulation thereof is known in the art (e.g. Krampera et al, Stem Cells. 2006 February; 24(2):386-98) and may be carried out by a person skilled in the art.

Antigen Stimulated Cells

In still another embodiment the MSC, regulatory T-cells and/or fibroblast cells may be stimulated with antigens prior to use in the method of the present invention. Antigen treatment of MSC for the stimulation thereof is known in the art and may be carried out by a person skilled in the art.

Mitomycin C Treated Msc.

In yet another embodiment the MSC, regulatory T-cells and/or fibroblast cells may be treated with Mitomycin C prior to use in the method of the present invention. Mitomycin C treatment of MSC is known in the art and may be carried out by a person skilled in the art.

Furthermore, it desired, the MSC, regulatory T-cells and/or fibroblast cells can be subjected to a combination of two or three of the treatments selected from the group consisting of irradiation, IFN-gamma stimulation and Mitomycin C treatment prior to use in the method of the present invention.

The maintenance conditions of said MSC can also contain cellular factors that allow cells to remain in an undifferentiated form. It is apparent to those skilled in the art that prior to differentiation, supplements that inhibit cell differentiation must be removed from the culture medium. It is also apparent that not all cells will require these factors. In fact, these factors may elicit unwanted effects, depending on the cell type.

Various embodiments of the invention will be illustrated by the following examples, which illustrate but do not limit the invention described herein.

Example 1

Evaluation of Lymphocyte biomarkers in USC Therapy Responders and Non-Responders.

Stem cell therapies have significant potential for use in the treatment of disorders characterized by tissue damage and inflammation. In order to identify blood-based markers having utility in determining patient prognosis for such therapies anal fistula in Crohn's patients is an ideal model disorder as it is characterized by tissue damage in a patient having an inflammatory disease. Lymphocyte analysis in patient blood samples was carried out both before and after treatment with allogeneic expanded adipose-derived cells (eASC).

Materials & Methods

Patient Population

The patient population consisted of 24 Crohn's patients having complex perianal fistula treated in a multicenter Phase I/II a clinical trial (clinicaltrials.gov identifier NCT01372969). Patients were treated with an intralesional administration of 20 million eASC. Fistula healing was determined 12 weeks post-treatment, and in case of incomplete healing a second dose of 40 million eASC was administered. Whole blood was collected from patients at two time points during the trial, baseline and 15 days.

An MRI was performed at baseline to assess collections >2 cm associated with the fistula tract. Subjects were followed for 24 weeks in total and healing was assessed at weeks 12 and 24 by means of radiological and clinical assessment.

Fistula closure at 12 weeks was used to define patients as responders (n=9), all other patients were defined as non-responders (n=15). Fistula closure was defined as the absence of suppuration of the fistula through the external orifice, both spontaneously and upon application of pressure, with complete reepithelization of the external orifice during clinical evaluation and absence of collections >2 cm, in three axis, directly related to the fistula tract treated, as measured by MRI. Fistulas were evaluated at two consecutive visits, i.e., weeks 10; 12 and 22; 24 to avoid misinterpretation and guide treatment decisions. Fistula evaluation was carried out by both the attending physician and an independent clinician. Table 1 provides an overview of the response status of each individual subject and the analysis carried out on their blood samples.

PEMC Isolation

Blood samples were collected from the patients at baseline and at 15 days. Peripheral blood mononuclear cells (PBMC) were isolated from the blood samples using Ficoll-paque Plus (GE Healthcare Biosciences AB, Uppsala, Sweden) following the supplier's protocol. Briefly, blood samples were diluted with balanced salt solution and Ficoll was added to create a density gradient. After centrifugation, the interface containing mononuclear cells was collected. Purity was verified by flow cytometry.

Mesenchymal Stem Cells

The allogeneic eASC medicinal product consisted of a cellular suspension of living adult stem cells of mesenchymal origin extracted from the subdermal adipose tissue of healthy donors. Subdermal adipose tissue was liposuctioned from the healthy donor and transported to the manufacturing facility. The donation, procurement, and testing were carried out according to the requirements of Directive 2004/23/EC and therefore under Directives 2006/17/EC and 2006/83/EC. ASCs were isolated by digesting the adipose tissue with 0.075% collagenase (Type I, Invitrogen, Carlsbad, Calif.), followed by centrifugation. The cell pellet obtained was resuspended and lysed in erythrocyte lysis solution (10% fetal bovine serum (FBS), treated with 160 mM $NH_4Cl$) and centrifuged. The stromal vascular fraction, resulting from the cell pellet was resuspended in culture medium (Dulbecco's modified Eagle medium; DMEM) with 10% FBS) and placed in cell culture containers in culture medium and antibiotics, and incubated at 37° C. and 5% CO2 and in a humidified atmosphere. At 24-48 h post-plating, the culture medium was removed to eliminate the non-attached cell fraction. ASCs adhered to the plastic culture plates that were expanded under in vitro conditions. Every 3-4 days, the culture medium was changed after reaching 90-95% confluence and the cells were detached with trypsin/EDTA, collected, centrifuged, and expanded without antibiotics to the required duplication. They were then harvested and cryopreserved until use. Before the appointed administration date, sufficient cryopreserved vials were thawed to provide the required dose for administration. ASCs were recovered from their cryopreserved state by plating and culturing (to confirm viability). On the day when the vials were filled and packaged, the cultures were washed with phosphate buffer solution, and trypsin/EDTA. The eASC were immediately resuspended in the selected excipients (Dulbecco modification Eagle medium and human albumin serum) to formulate the drug product.

Flow Cytometry.

Antibodies against CD3, CD4, CD8, CD25, FOXP3, HLA-II, (BD Bioscience) labelled with different fluorochromes were used. Isotype controls were from BD Bioscience. Cells were harvested and stained with the appropriate surface monoclonal antibodies following manufacturer instructions. After washing, cells were fixed and $10 \times 10^3$ events were acquired using a FACSCanto (BD Bioscience). FACS Diva software was used for acquisition and analysis.

Immnophenotyping of Circulating T Cells

The cellular repertoire in peripheral blood from the patients was studied at baseline and at 15 days. The peripheral blood mononuclear fraction was selected for the phenotypic analysis of the T (defined by CD3+), helper T cells (Defined by CD3+CD4+), and cytotoxic T cells (defined by CD3+CD8+).

Lymphocyte HLA-II Expression

Expression levels of HLA II upon in vitro co-culture of the patient PBMC samples with the allogeneic eASC of the medicinal product were determined as an indicator of in-vivo immune recognition of the donor eASC. Briefly, eASC were seeded in a 96-well plate ($3 \times 10^3$) and cultured for 24 hours, alone or in the presence of PBMCS ($2 \times 10^5$) from each of the patients in the trial. After culture cells were harvested and FACS analysis was performed. Monoclonal antibodies against CD3 and HLA II, were used to measure HLA II expression on T cells after the in-vitro incubation with or without eASCs (control).

Statistics

Paired Student's t-test was used to analyze statistic difference. The p-values less than 0.05 were considered as significant.

Results

T Cell Immunophenotype

Circulating cell repertoire of the participants of the study was analyzed by flow cytometry. Percentage of distribution of T cells (CD3+ population in the lymphocyte region), helper T cells, cytotoxic T cells and regulatory T cells was studied in isolated PBMCs in the groups of responder and non responder patients in the samples collected before being treated with eASCs.

Variations in the T cell compartment were observed between the responder and non-responder groups. As shown in FIG. 1 the responder group presented lower levels of CD4 T ($45.2 \pm 5\%$ of the CD3+ cell population) cells and higher levels of CD8 ($54.8 \pm 5\%$ of the CD3+ cell population) T cells than the non responder population. The non-responder group presented a relatively normal distribution of CD4 and CD8 T cells ($34.99 \pm 7\%$ of CD8 and $65.01 \pm 7\%$ of CD4 of the total CD3+ cell population). Accordingly cut-off values in the range of 45% to 65%, more preferably 50%-60% CD8+ lymphocytes and 35% to 55%, more preferably 40% to 50% CD4+ lymphocytes is suitable for discriminating between the responder and non-responder populations.

Figure 2:
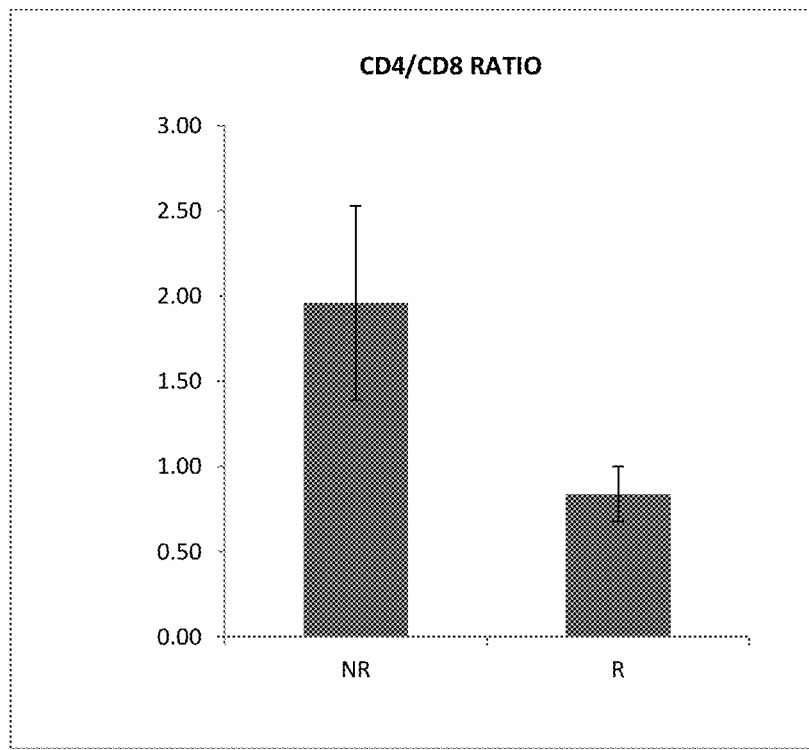
FIG. 2: CD4:CD8 ratio in patient PBMC in responder and non-responder groups at baseline

As an alternative means of expressing these values the CD4:CD8 ratio was calculated and is provided in FIG. 2. This data showed that the non-responder population had a mean CD4:CD8 ratio over 1.5, however the responder population, due to the increase of the cytotoxic cell compartment and the decreased helper population have a mean ratio below 1.5 indicating that this group of patients had a more immune activated profile.

Lymphocyte HILA-II Expression

Figure 3:
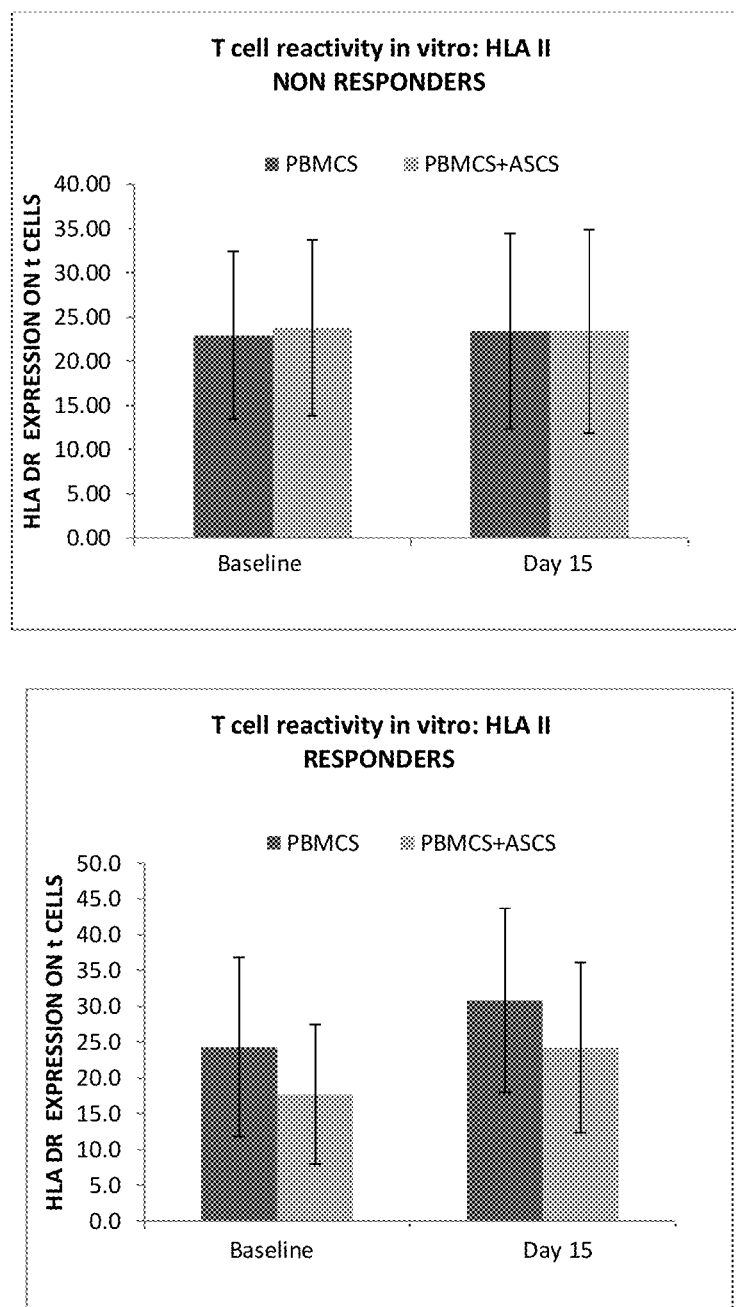
FIG. 3: HLA-II expression in patient PBMC at baseline and Day 15 PBMC in responder and non-responder groups

Expression levels of HLA II upon in vitro co-culture of the volunteer PBMC samples (both pre- and post-eASC treatment) with the allogeneic donor eASC were studied. HLA II is an indication of in-vivo immune recognition of the donor eASC. Percentage expression of the HLA-II marker is provided in FIG. 3. It was demonstrated that patients in the responder group had a significant down-regulation of HLA-II expression. At baseline in the non-responder group mean HLA-II expression was 22.93 with a standard deviation of +/−9.5 in PBMC and a mean of 23.77 with standard deviation +/−9.91 for co-cultured PBMC+ASCS. In the responder group mean HLA-II expression was 24.35+/−12.51 in PBMC, which surprisingly decreased to 17.73 with a standard deviation of +/−9.71 in the co-cultured PBMC+ASCS.

Furthermore, this down-regulation was also observed at day 15 indicating that the HLA-II marker may be used in determining clinical response both prior to and during the early stages of treatment.

TABLE 1

| Patient | Treatment Response | CD4 Assay | CD8 Assay | HLA-II Assay |
|---|---|---|---|---|
| 1 | Non-responders | ✓ | ✓ | ✓ |
| 2 | | ✓ | ✓ | ✓ |
| 3 | | X | x | ✓ |
| 4 | | ✓ | ✓ | ✓ |
| 5 | | ✓ | ✓ | ✓ |
| 6 | | X | x | ✓ |
| 7 | | ✓ | ✓ | ✓ |
| 8 | | ✓ | ✓ | ✓ |
| 9 | | ✓ | ✓ | ✓ |
| 10 | | X | x | ✓ |
| 11 | | ✓ | ✓ | ✓ |
| 12 | | ✓ | ✓ | ✓ |
| 13 | | ✓ | ✓ | ✓ |
| 14 | | ✓ | ✓ | ✓ |
| 15 | | ✓ | ✓ | ✓ |
| 16 | Responders | X | x | ✓ |
| 17 | | ✓ | ✓ | ✓ |
| 18 | | ✓ | ✓ | ✓ |
| 19 | | ✓ | ✓ | ✓ |
| 20 | | ✓ | ✓ | ✓ |
| 21 | | X | x | ✓ |
| 22 | | ✓ | ✓ | ✓ |
| 23 | | ✓ | ✓ | ✓ |
| 24 | | ✓ | ✓ | ✓ |

The invention claimed is:

1. A method for predicting a clinical response and treating a human subject suffering from a fistula, an autoimmune disease, or an immune-mediated inflammatory disease with a pharmaceutical composition comprising adipose-derived stromal and/or mesenchymal stem cells, the method comprising
   i) obtaining a blood sample from said human subject;
   ii) evaluating a lymphocyte marker in said blood sample obtained from said human subject, wherein said lymphocyte marker is selected from the group comprising the CD4+ lymphocyte level, the CD8+ lymphocyte level, the lymphocyte HLA-II level and combinations thereof;
   iii) determining whether the human subject is a responder to said pharmaceutical composition, wherein the human subject is classified as a responder if:
      (a) the human subject has a CD4+ level equal to a value in the range of 40% to 50% of the total T-lymphocytes;
      (b) the human subject has a CD8+ level equal to a value in the range of 50% to 60% of the total T-lymphocytes;
      (c) the human subject has a CD4+:CD8+ cell ratio equal to a value in the range of 1.0 to 0.7;
      or if
      (d) the human subject has a reduction in lymphocyte HLA-II level by at least 10% relative to a reference value after contact with allogeneic mesenchymal stem cells; and
   (iv) administering said pharmaceutical composition only to the responder human subject.

2. A method according to claim 1, wherein the stem cells are allogeneic stem cells.

3. A method for treating a human subject suffering from a fistula, an autoimmune disease, or an immune-mediated inflammatory disease, wherein a blood sample from the human subject has previously been tested to evaluate a lymphocyte marker in said blood sample obtained from said human subject; wherein said lymphocyte marker is selected from the group comprising the CD4+ lymphocyte level, the CD8+ lymphocyte level, the lymphocyte HLA-II level and combinations thereof, wherein the human subject has been determined to be a responder to a pharmaceutical composition if the human subject has:
   (a) a CD4+ level equal to a value in the range of 40% to 50% of the total T-lymphocytes;
   (b) a CD8+ level equal to a value in the range of 50% to 60% of the total T-lymphocytes;
   (c) a CD4+:CD8+ cell ratio equal to a value in the range of 1.0 to 0.7; or
   (d) a reduction in lymphocyte HLA-II level by at least 10% relative to a reference value after contact with allogeneic mesenchymal stem cells, and
   wherein only the responder human subject is treated with a pharmaceutical composition comprising adipose-derived stromal and/or mesenchymal stem cells.

4. The method according to claim 1, wherein the fistula is selected from an anal fistula or a rectovaginal fistula.

5. The method according to claim 1, wherein the fistula is an anal fistula.

6. The method according to claim 1, wherein the fistula is an anal fistula in a patient with Crohn's disease.

7. The method according to claim 1, wherein the lymphocyte HLA-II level is considered reduced when levels are reduced by at least 5%, relative to a reference value.

8. The method according to claim 7, wherein the reference value is a HLA-II level in a sample of non-stimulated lymphocytes.

9. The method according to claim 8, wherein the sample is from the human subject or from lymphocytes pooled from blood of a population of two or more individuals.

10. The method according to claim 3, wherein the fistula is selected from an anal fistula or a rectovaginal fistula.

11. The method according to claim 3, wherein the fistula is an anal fistula.

12. The method according to claim 3, wherein the fistula is an anal fistula in a patient with Crohn's disease.

13. The method according to claim 3, wherein the lymphocyte HLA-II level is considered reduced when levels are reduced by at least 5%, relative to a reference value.

14. The method according to claim 13, wherein the reference value is a HLA-II level in a sample of non-stimulated lymphocytes.

15. The method according to claim 14, wherein the sample is from the human subject or from lymphocytes pooled from blood of a population of two or more individuals.

16. A method for predicting a clinical response and treating a human subject suffering from a fistula, an autoimmune disease, or an immune-mediated inflammatory disease, excluding rejection of transplanted organs and tissues, with a pharmaceutical composition comprising adipose-derived stromal and/or adipose-derived mesenchymal stem cells, the method comprising
   i) obtaining a blood sample from said human subject;
   ii) evaluating a lymphocyte marker in said blood sample obtained from said human subject, wherein said lymphocyte marker is selected from the group comprising the CD4+ lymphocyte level, the CD8+ lymphocyte level, the lymphocyte HLA-II level and combinations thereof;

iii) determining whether the human subject is a responder to said pharmaceutical composition, wherein the human subject is classified as a responder if:
   (a) the human subject has a CD4+ level equal to a value in the range of 40% to 50% of the total T-lymphocytes;
   (b) the human subject has a CD8+ level equal to a value in the range of 50% to 60% of the total T-lymphocytes;
   (c) the human subject has a CD4+:CD8+ cell ratio equal to a value in the range of 1.0 to 0.7 or if
   (d) the human subject has a reduction in lymphocyte HLA-II level by at least 10% relative to a reference value after contact with allogeneic mesenchymal stem cells; and (iv) administering said pharmaceutical composition only to the responder human subject.

* * * * *